United States Patent
Leimbach et al.

(10) Patent No.: US 10,090,616 B1
(45) Date of Patent: Oct. 2, 2018

(54) SURGICAL INSTRUMENT HANDLE ASSEMBLY WITH FEATURE TO CLEAN ELECTRICAL CONTACTS AT MODULAR SHAFT INTERFACE

(71) Applicant: ETHICON LLC, Guaynabo, PR (US)

(72) Inventors: Richard L. Leimbach, Cincinnati, OH (US); Shane Adams, Lebanon, OH (US); Ryan P. Posey, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/634,589

(22) Filed: Jun. 27, 2017

(51) Int. Cl.
| H01R 13/52 | (2006.01) |
| A61B 17/00 | (2006.01) |
| A61B 17/072 | (2006.01) |
| A61B 17/115 | (2006.01) |

(52) U.S. Cl.
CPC ... *H01R 13/5224* (2013.01); *A61B 17/00234* (2013.01); *H01R 13/5219* (2013.01); *H01R 13/5227* (2013.01); *A61B 17/072* (2013.01); *A61B 17/07207* (2013.01); *A61B 17/1155* (2013.01); *A61B 2017/0046* (2013.01); *A61B 2017/00464* (2013.01); *A61B 2017/00734* (2013.01); *A61B 2017/00938* (2013.01)

(58) Field of Classification Search
CPC ............ H01R 13/5224; H01R 13/5219; H01R 13/5227
USPC .......................................................... 439/271
See application file for complete search history.

(56) References Cited

U.S. PATENT DOCUMENTS

| 4,284,312 | A | * | 8/1981 | Patchett | ............. | H01R 13/5219 439/281 |
| 5,684,689 | A | * | 11/1997 | Hahn | ................. | H01R 13/6675 363/146 |
| 5,980,289 | A | * | 11/1999 | Engle | ................... | H01R 13/005 439/195 |
| 6,181,032 | B1 | * | 1/2001 | Marshall | ................... | B25F 3/00 200/321 |
| 6,783,524 | B2 | * | 8/2004 | Anderson | ...... | A61B 17/320068 606/1 |
| 7,000,818 | B2 | | 2/2006 | Shelton, IV et al. | | |
| 7,320,614 | B2 | * | 1/2008 | Toda | .................... | H01R 13/658 439/358 |
| 7,380,696 | B2 | | 6/2008 | Shelton, IV et al. | | |

(Continued)

OTHER PUBLICATIONS

U.S. Appl. No. 15/634,385, filed Jun. 27, 2017.

(Continued)

*Primary Examiner* — Alexander Gilman
(74) *Attorney, Agent, or Firm* — Frost Brown Todd LLC

(57) ABSTRACT

A powered surgical instrument includes a shaft assembly and a handle assembly. The shaft assembly includes a first electrical connector and a flexible element positioned adjacent to the first electrical connector. The handle assembly includes a second electrical connector. The handle assembly is configured to attach to the shaft assembly. The second electrical connector is configured to electrically connect with the first electrical connector when the handle assembly is attached to the shaft assembly. The flexible element is configured to create a liquid-resistant seal against the handle assembly and adjacent to the electrical connection of the first and second electrical connectors when the shaft assembly and the handle assembly are attached.

19 Claims, 9 Drawing Sheets

(56) References Cited

U.S. PATENT DOCUMENTS

| | | | |
|---|---|---|---|
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,857,647 B2 * | 12/2010 | Bracci | H01R 13/5205 439/274 |
| 8,408,439 B2 | 4/2013 | Huang et al. | |
| 8,453,914 B2 | 6/2013 | Laurent et al. | |
| 9,072,535 B2 | 7/2015 | Shelton, IV et al. | |
| 9,186,142 B2 | 11/2015 | Fanelli et al. | |
| 9,381,288 B2 * | 7/2016 | Schenck | A61M 5/142 |
| 9,675,739 B2 * | 6/2017 | Tanner | A61M 1/101 |
| 9,717,497 B2 | 8/2017 | Zerkle et al. | |
| 9,743,929 B2 * | 8/2017 | Leimbach | A61B 17/07207 |
| 9,795,379 B2 | 10/2017 | Leimbach et al. | |
| 9,808,248 B2 | 11/2017 | Hoffman | |
| 9,827,356 B2 * | 11/2017 | Muller | A61M 1/1008 |
| 2012/0021653 A1 * | 1/2012 | Chen | H01R 13/639 439/655 |
| 2014/0263541 A1 | 9/2014 | Leimbach et al. | |
| 2015/0272575 A1 | 10/2015 | Leimbach et al. | |
| 2015/0280384 A1 | 10/2015 | Leimbach et al. | |
| 2016/0062125 A1 * | 3/2016 | Baek | G02B 27/0176 361/679.01 |
| 2016/0087381 A1 * | 3/2016 | Wong | H01R 13/73 439/529 |
| 2016/0097525 A1 * | 4/2016 | Chien | F21V 33/004 362/135 |
| 2016/0098891 A1 * | 4/2016 | Eby | G07F 17/3216 463/16 |
| 2016/0099596 A1 * | 4/2016 | Chien | H02J 7/0052 368/10 |
| 2016/0104972 A1 * | 4/2016 | Feng | H01R 13/6581 439/607.27 |
| 2016/0249917 A1 | 9/2016 | Beckman et al. | |
| 2016/0256162 A1 * | 9/2016 | Shelton, IV | A61B 17/072 |
| 2017/0086823 A1 | 3/2017 | Leimbach et al. | |

OTHER PUBLICATIONS

U.S. Appl. No. 15/634,418, filed Jun. 27, 2017.
U.S. Appl. No. 15/634,436, filed Jun. 27, 2017.
U.S. Appl. No. 15/634,452, filed Jun. 27, 2017.
U.S. Appl. No. 15/634,475, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,620, filed Jun. 27, 2017.

* cited by examiner

SURGICAL INSTRUMENT HANDLE ASSEMBLY WITH FEATURE TO CLEAN ELECTRICAL CONTACTS AT MODULAR SHAFT INTERFACE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, now U.S. Pat. No. 9,186,142, issued Nov. 17, 2015; U.S. Patent Application Publication No. 2014/0239041, entitled "Lockout Feature for Movable Cutting Member of Surgical Instrument," Published Aug. 28, 2014, now U.S. Pat. No. 9,717,497, issued Aug. 1, 2017; U.S. Patent Application Publication No. 2014/0239038, entitled "Surgical Instrument with Multi-Diameter Shaft," published Aug. 28, 2014, now U.S. Pat. No. 9,795,379, issued Oct. 24, 2017; and U.S. Patent Application Publication No. 2014/0239044, entitled "Installation Features for Surgical Instrument End Effector Cartridge," published Aug. 28, 2014, now U.S. Pat. No. 9,808,249, issued Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
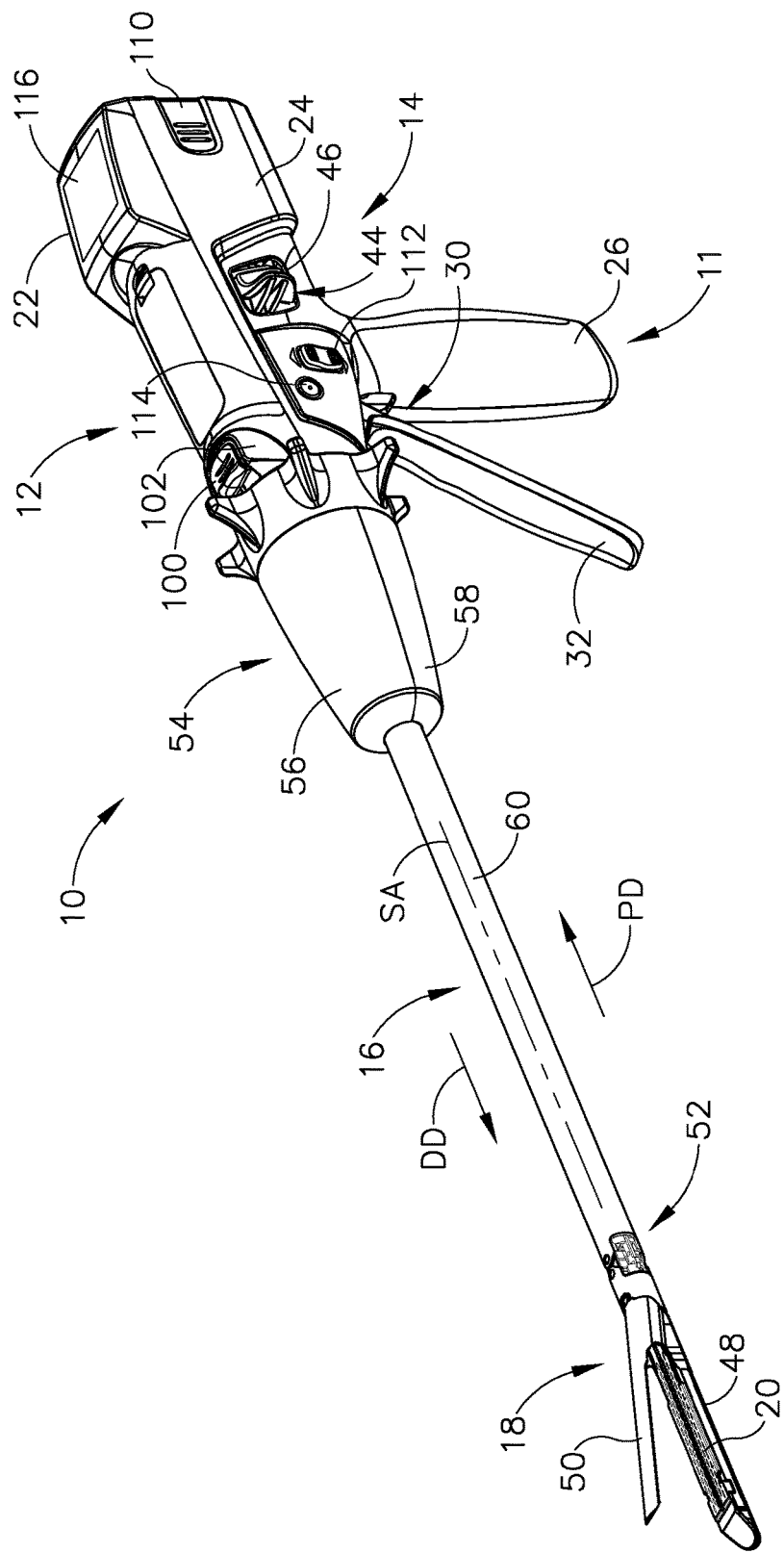
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
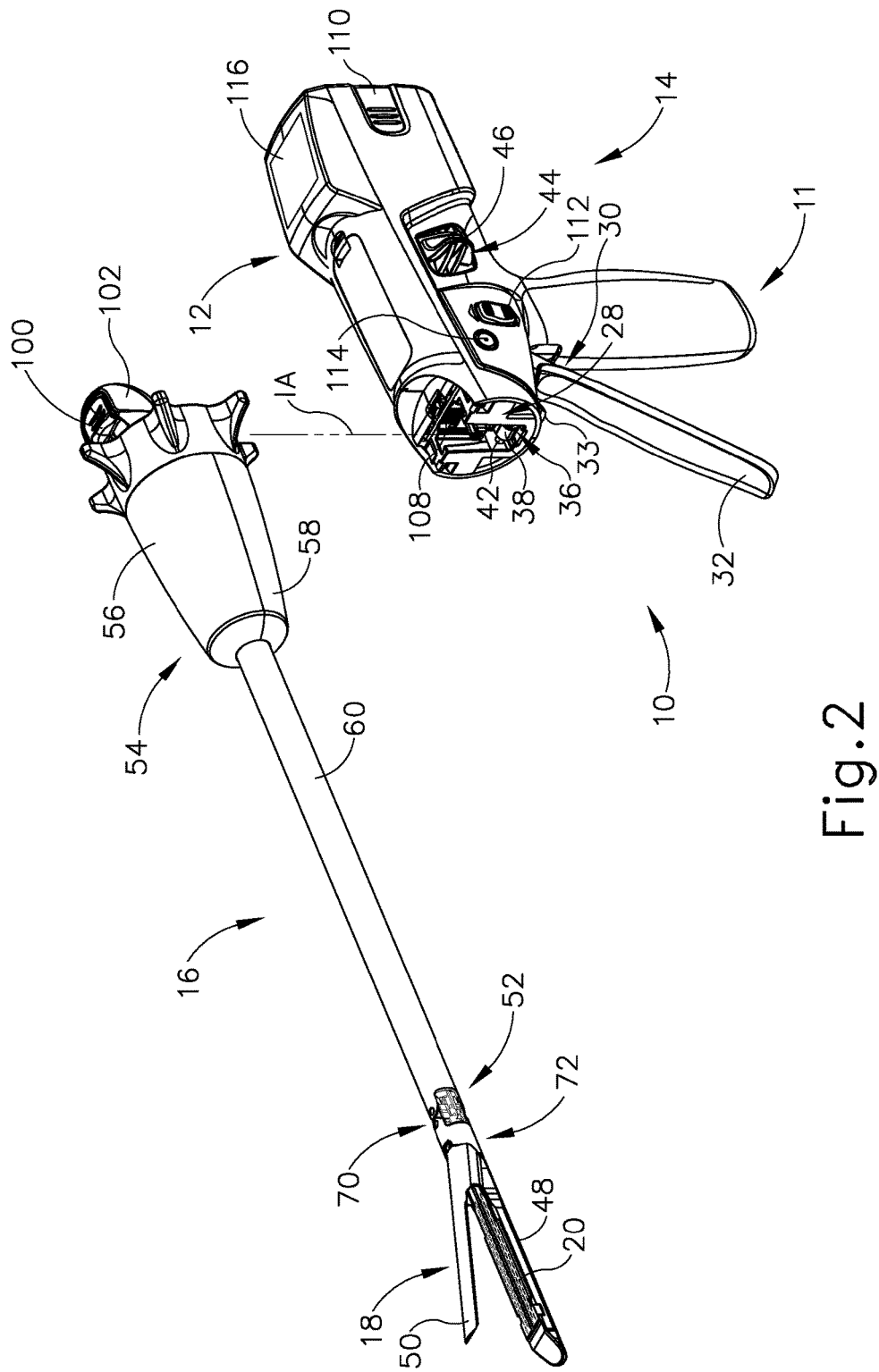
FIG. 2 depicts a perspective view of the instrument of FIG. 1, showing the shaft assembly disassembled from the handle assembly of the instrument.
Figure 3:
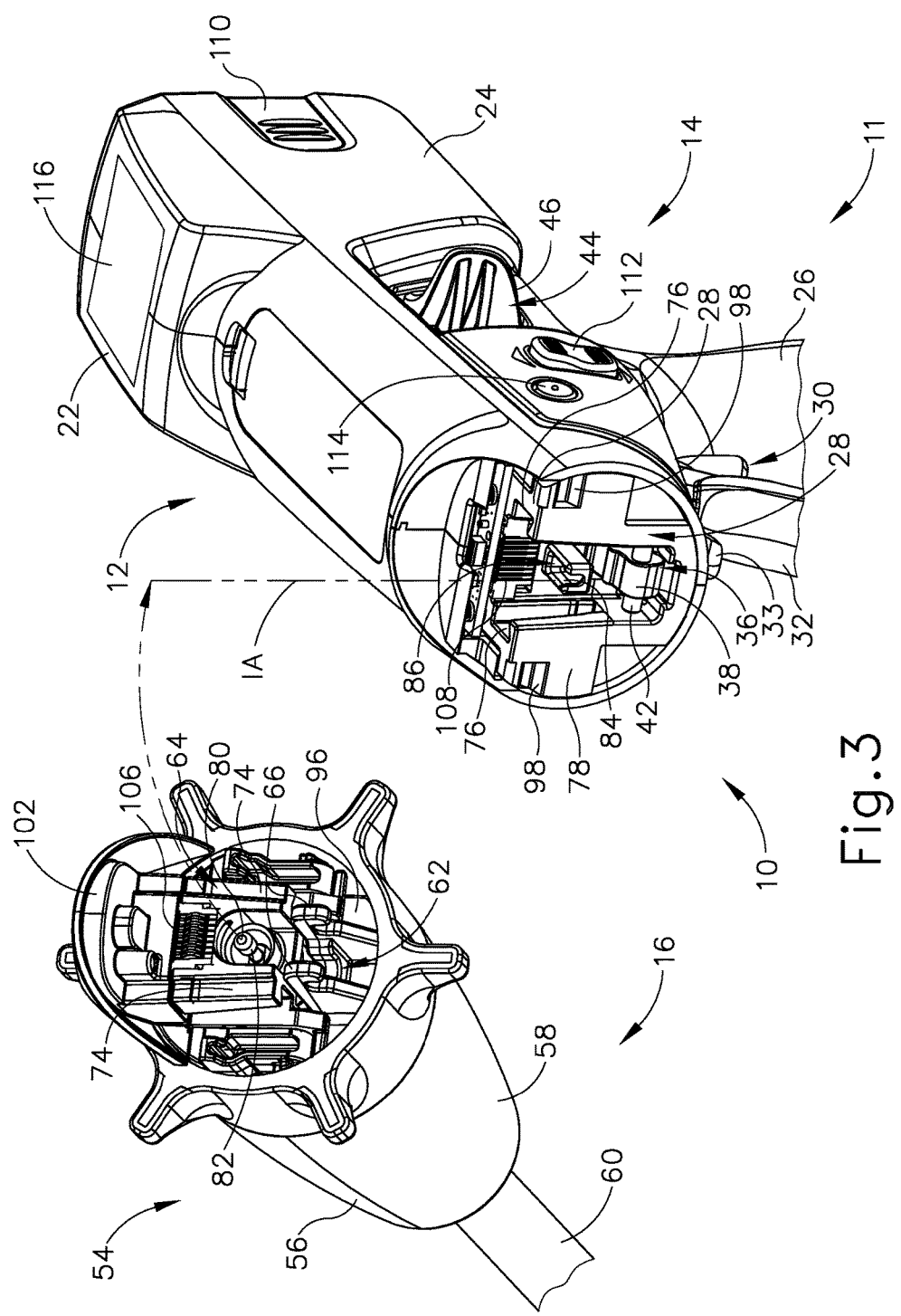
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
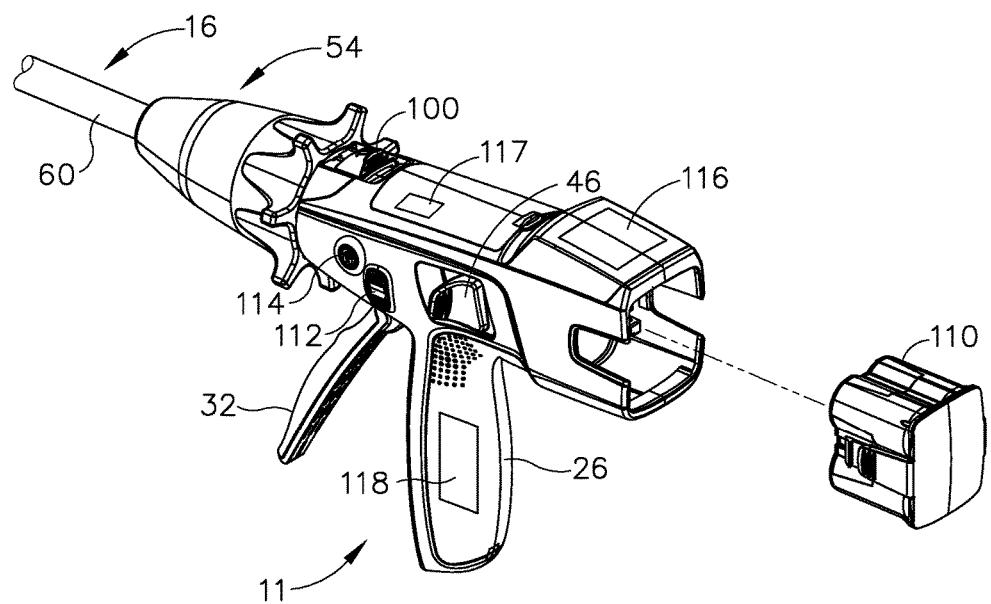
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein.

Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, now U.S. Pat. No. 9,913,642, issued Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, the disclosure of which is incorporated by reference herein; and/or in accordance with the teachings of various other references cited herein.

Figure 4A:
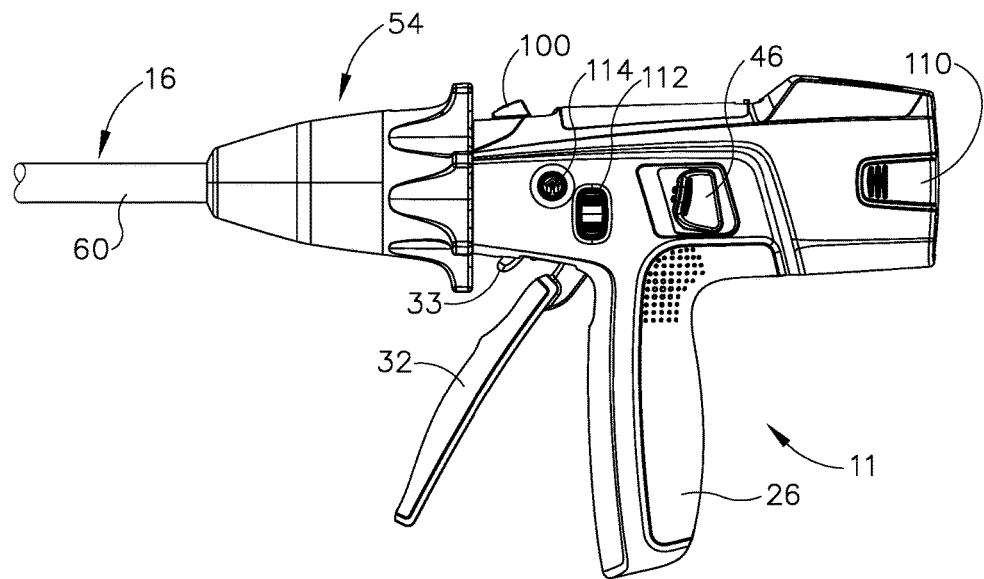
FIG. 4A depicts a side elevational view of a proximal portion of the instrument of FIG. 1, with a closure trigger in a first pivotal position and a firing trigger in a first pivotal position.
Figure 4B:
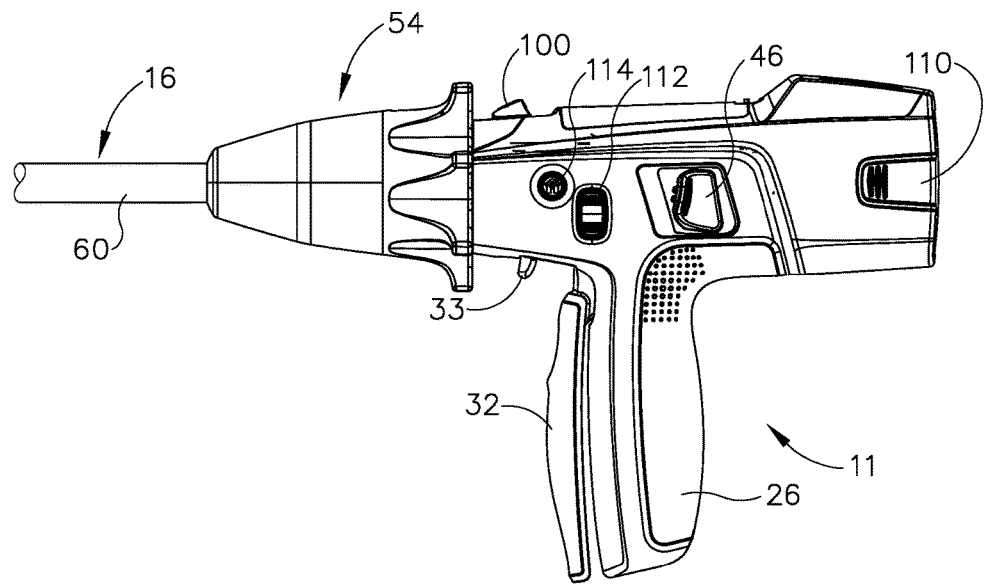
FIG. 4B depicts a side elevational view of a proximal portion of the instrument of FIG. 1, with the closure trigger in a second pivotal position and the firing trigger in a second pivotal position.
Figure 4C:
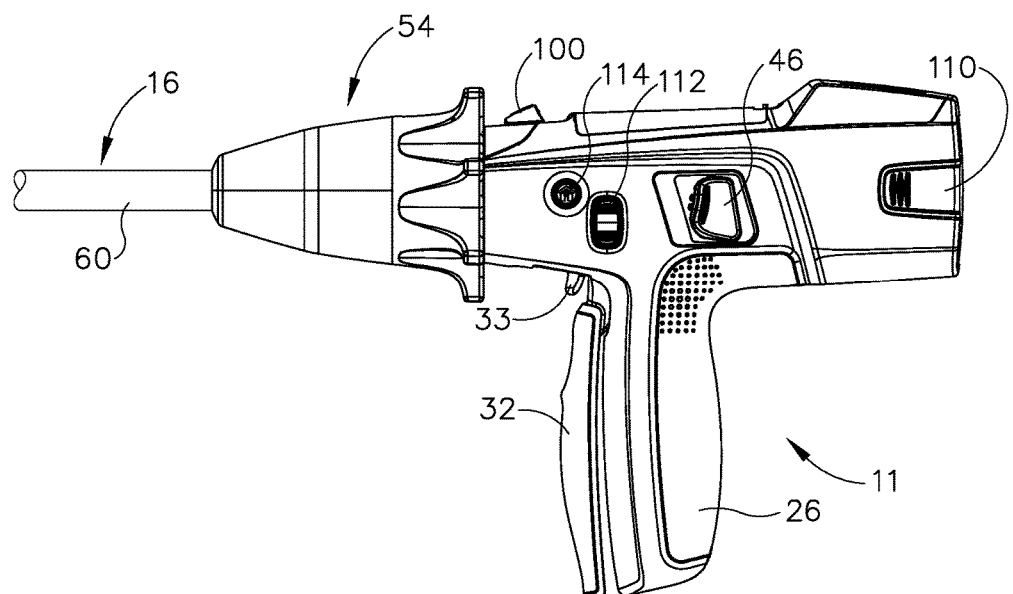
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, the disclosure of which is incorporated by reference herein; in accordance with at least some of the teachings of U.S. Pub. No. 2015/0280384, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively coupled with an electrical circuit of shaft assembly (16). Electrical connector (106) is configured for mating engagement with a corresponding electrical connector (108) that is coupled with control circuit (117). In the present example, connectors (106, 108) are in the form of conductive electrical contacts that are complementarily configured and positioned to engage each other when shaft assembly (16) is coupled with handle (14). In addition, connectors (106) are resiliently biased to project proximally relative to the rest of shaft assembly (16). Further details regarding the circuitry and control systems may be found in U.S. Pub. No. 2014/0263541, the disclosure of which is incorporated by reference herein and/or U.S. Pub. No. 2015/0272575, now U.S. Pat. No. 9,913,642, issued Mar. 13, 2018, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
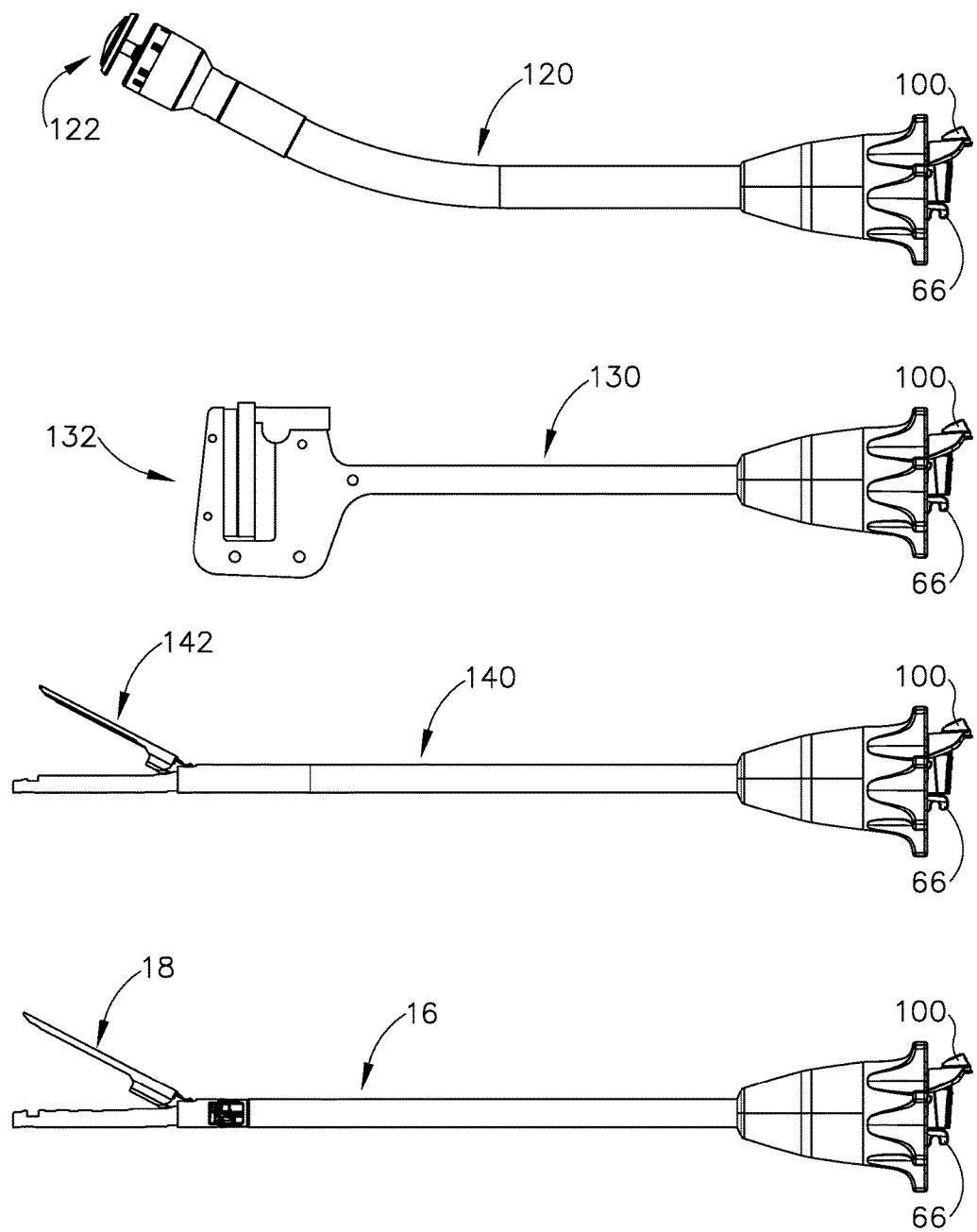
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, now U.S. Pat. No. 9,913,642, issued Mar. 13, 2018, the disclosure of which is incorporated by reference herein. In addition or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. Exemplary Surgical Instrument with Seal Feature

In some instances, it may be beneficial for the electrical connectors (106, 108) of a powered surgical instrument (10) commonly used in procedures where liquid may reach the electrical connectors (106, 108) to be protected from liquid exposure. In particular, the interface between the shaft assembly (16) and handle assembly (11) of surgical instrument (10) includes electrical connectors (106, 108) that are essential to the performance of the surgical instrument (10). The introduction of fluid to these connections (106, 108) may create short circuits, prevent proper contact between the connectors (106, 108), or otherwise adversely affect the electrical linkage between the respective circuits of the shaft assembly (16) and handle assembly (11), thus degrading the functionality of surgical instrument (10). Including a flexible or compressible element adjacent to electrical connectors (106, 108) of surgical instrument (10) may be beneficial to protect the electrical contacts from potential liquid exposure. The flexible or compressible element may also serve to clean the electrical connectors (106, 108) when the shaft assembly (16) and handle assembly (11) of surgical instrument (10) are coupled together.

While the following example is provided in the context of instrument (10) described above, the below teachings may be readily applied to various other kinds of instruments. By way of example only, the below teachings may be readily applied to the instruments described in U.S. Pub. No. 2015/0280384, the disclosure of which is incorporated by reference herein. By way of further example only, the below teachings may be readily applied to the instruments described in U.S. Pub. No. 2016/0249917, the disclosure of which is incorporated by reference herein. Other kinds of instruments to which the below teachings may be applied will be apparent to those of ordinary skill in the art.

Figure 7:
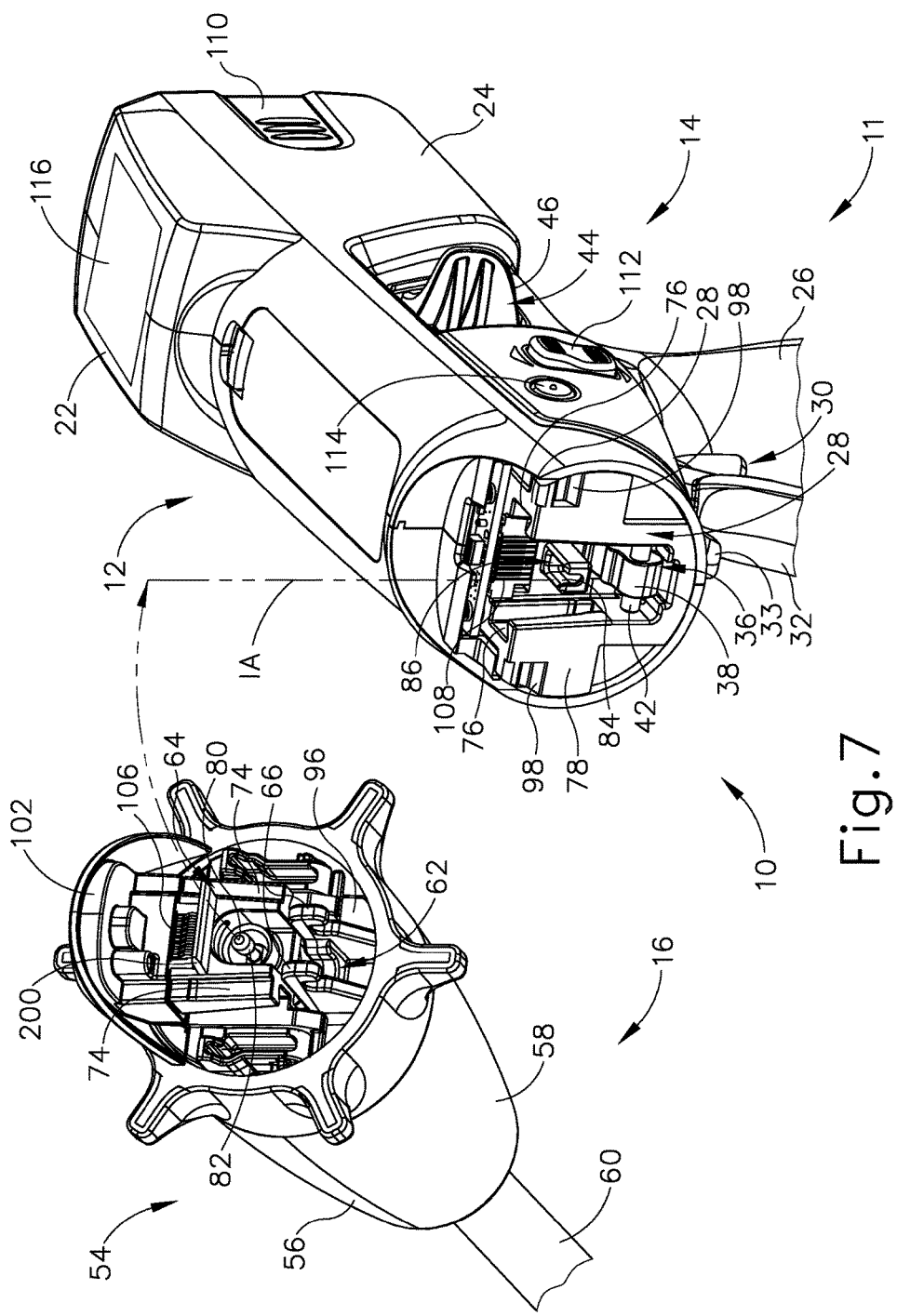
FIG. 7 depicts a partial perspective view of an exemplary variation of the instrument of FIG. 1, showing the shaft assembly disassembled from the handle assembly of the instrument, the shaft assembling including a wiper seal.
Figure 8:
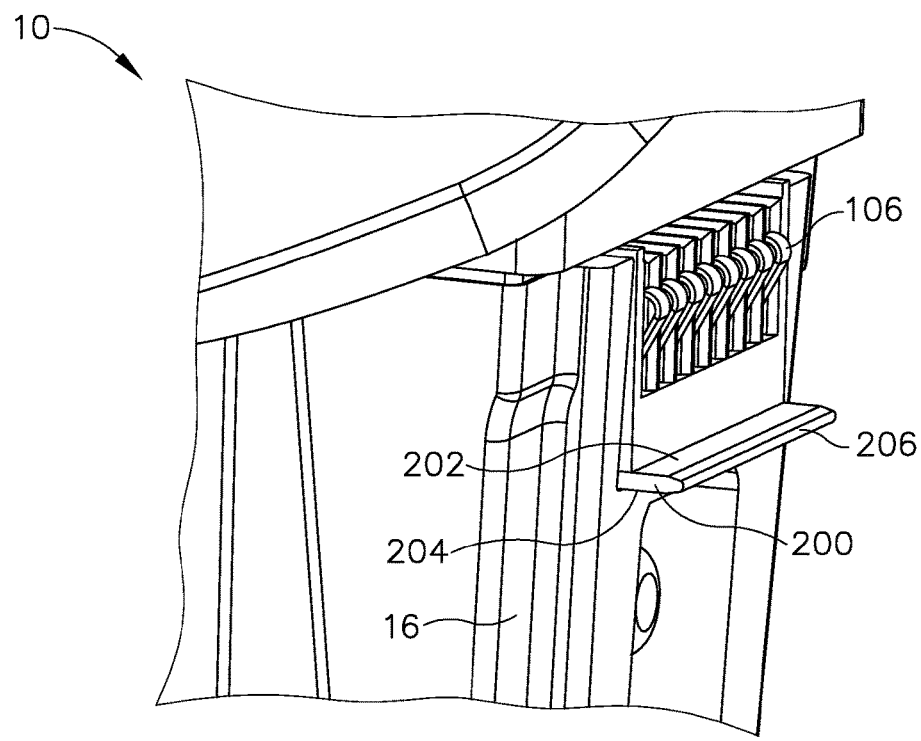
FIG. 8 depicts a partial perspective view of the proximal end of the shaft assembly of FIG. 7.
Figure 9:
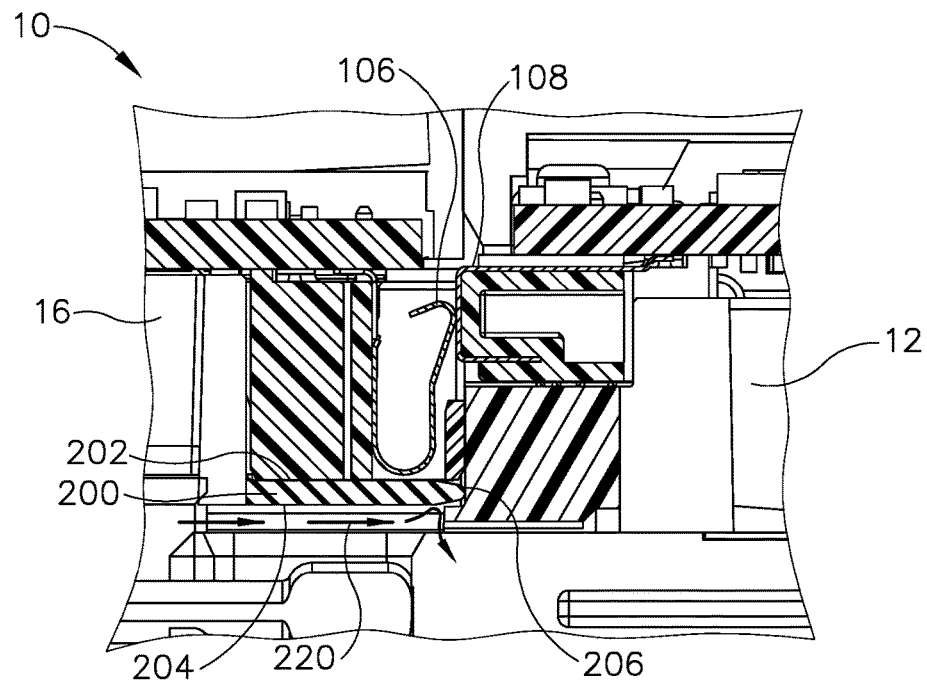
FIG. 9 depicts a cross sectional view of the instrument of FIG. 7, with the shaft assembly assembled with the handle assembly, showing the resulting flow path of fluid ingress due to the position of the wiper seal.
Figure 10:
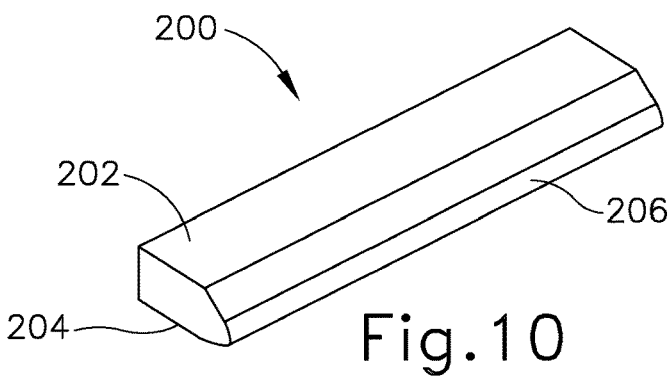
FIG. 10 depicts a perspective view of the exemplary wiper seal of the instrument of FIG. 7, the wiper seal having a chamfered or rounded profile.

FIGS. 7-9 illustrate an exemplary wiper (200) installed on an exemplary variation of surgical instrument (10) as described above, except for the teachings explicitly detailed below. Wiper (200) is located on proximal housing or nozzle (54) of shaft assembly (16). Wiper (200) is positioned on chassis (64) of shaft assembly (16) and has a lateral length extending between tapered attachment portions (74). Wiper (200) is configured to extend proximally from chassis (64) at a length that permits tapered attachment portion (74) and wiper (200) to be received and tightly fit within corresponding dovetail slots (76) of handle assembly (11). Wiper (200) is positioned adjacently beneath electrical connector (106)

and directly above shaft attachment lug (80) of shaft assembly (16). Although not shown, it should be understood that wiper (200) may be similarly situated at varying positions on handle assembly (11) as will be apparent to those of ordinary skill in the art. As seen in FIG. 10, wiper (200) includes top surface (202), bottom surface (204), and extending edge (206). Top surface (202) is positioned opposite of bottom surface (204) and faces electrical connector (106) of shaft assembly (16), whereas bottom surface (204) faces shaft attachment lug (80) of shaft assembly (16). Top surface (202) is separated from bottom surface (204) by a thickness of extending edge (206).

Wiper (200) is configured to create a fluid-impermeable seal between top surface (202) and bottom surface (204) to thereby inhibit fluid communication between top surface (202) and bottom surface (204). Wiper (200) is formed of an elastomeric material (e.g., rubber, silicone, etc.) that is configured to be laterally compressible when contacting edge (206) is tightly fitted against an interface surface of handle assembly (11) directly beneath electrical connector (108) to create a fluid-impermeable seal between wiper (200) and housing (12). Wiper (200) is further formed of a hydrophobic material that is configured to repel water along top surface (202) and bottom surface (204). As it will be apparent to those of ordinary skill in the art in view of the teachings herein, wiper (200) may be formed of various suitable materials that provide compressive capabilities for contacting edge (206) and water resistant surfaces along top surface (202) and bottom surface (204). It should be understood that wiper (200) may also be coated with a hydrophobic material to thereby provide suitable liquid resistant characteristics along top surface (202), bottom surface (204) and contacting edge (206).

In the present example, shaft assembly (16) is configured for operative attachment to housing (12) as described above. Furthermore, electrical connector (106) of shaft assembly (16) is configured for mating engagement with corresponding electrical connector (108) of handle assembly (11). As seen in FIG. 8, upon attachment of shaft assembly (16) to housing (12), wiper (200) creates a mechanical barrier beneath the mating engagement of electrical connectors (106, 108) and above the coupling of shaft attachment lug (80) and firing shaft attachment cradle (84). Contacting edge (206) serves to create a fluid-impermeable seal between wiper (200) and an interface surface of handle assembly (11) directly beneath electrical connector (108). The seal created by wiper (200) effectively inhibits any fluid ingress below wiper (200) from contacting electrical connectors (106, 108).

As previously mentioned, electrical connector (106) is operatively coupled with an electrical circuit of shaft assembly (16). Further, electrical connector (108) is operatively connected to control circuit (117) of housing (12). Control circuit (117) is configured to receive and process one or more signals from the electrical circuit of shaft assembly (16) once shaft assembly (16) is operatively engaged with handle (14). By creating a seal between top surface (202) and bottom surface (204), wiper (200) protects the electrical communication between the electrical circuit of shaft assembly (16) and control circuit (117) through the mechanical barrier which serves to isolates electrical connectors (106, 108) from the remaining interface of shaft assembly (16) and handle assembly (11) beneath bottom surface (204). Without wiper (200), electrical connectors (106, 108) may otherwise be exposed to fluid and/or other debris that may hinder the capability of control circuit (117) to communicate with the electrical circuit of shaft assembly (16) through electrical connectors (106, 108) and thereby render surgical instrument (10) wholly inoperable.

FIG. 9 displays an anticipated path of fluid ingress (220) in surgical instrument (10) at the interface of shaft assembly (16) and handle assembly (11). Due to the presence of wiper (200) beneath electrical connector (106), the path of fluid ingress (220) is forced to redirect its route once encountering bottom surface (204) of wiper (200). Due to the fluid-impermeable seal created by contacting edge (206) between wiper (200) and the corresponding interface surface of handle assembly (11) directly beneath electrical connector (108), fluid ingress (220) is forced to travel in a direction opposite and away from wiper (200) and thereby away from electrical connectors (106, 108).

In the present example, wiper (200) may further serve as a wiping feature for surgical instrument (10). Contacting edge (206) is configured to contact electrical connector (108) of housing (12) when shaft assembly (16) is coupled to housing (12) and similarly when shaft assembly (16) is uncoupled from housing (12). Due to the positioning of wiper (200) adjacently beneath electrical connector (106) and directly above shaft attachment lug (80), and in conjunction with the proximal extension of wiper (200) from chassis (64), contacting edge (206) may regularly press against electrical connector (108) and thereby wipe along electrical connector (108) when shaft assembly (16) is coupled to housing (12) and similarly when shaft assembly (16) is uncoupled from housing (12). By pressing against electrical connector (108) during the installation and deinstallation of shaft assembly (16) to housing (12), contacting edge (207) may provide a cleaning and/or wiping functionality to electrical connector (108) to thereby remove any fluid and/or debris that may be present on electrical connector (108) prior to its electrical linkage to electrical connector (106) of shaft assembly (16). Contacting edge (206) may be further formed of an absorptive material to thereby absorb any fluid and/or other debris that may be present on electrical connector (108) as contacting edge (206) passes against electrical connector (108) when shaft assembly (16) is attached to housing (12).

Figure 11:
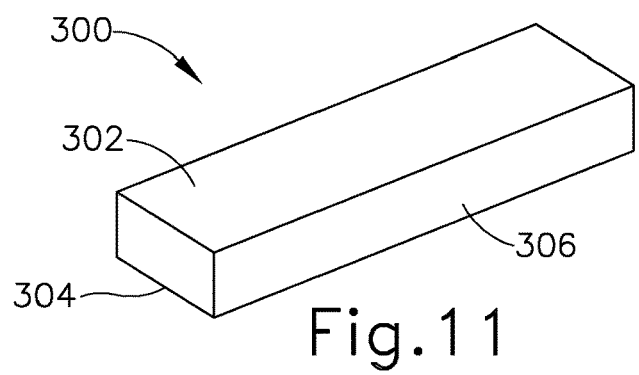
FIG. 11 depicts a perspective view of an exemplary alternative wiper seal that may be incorporated into the instrument of FIG. 7, the wiper seal having a squared profile.
Figure 12:
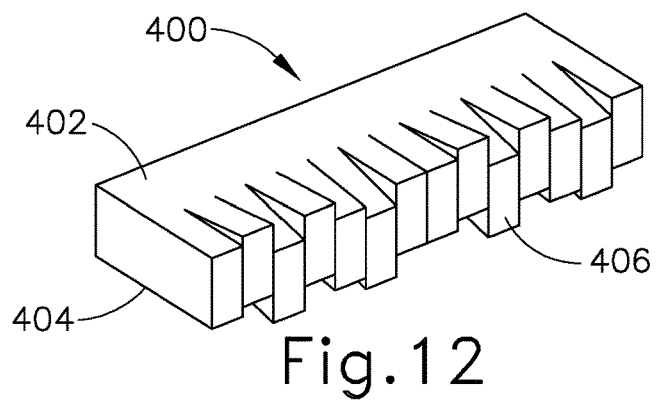
FIG. 12 depicts a perspective view of another exemplary alternative wiper seal that may be incorporated into the instrument of FIG. 7, the wiper seal having a grossly-bristled edge.
Figure 13:
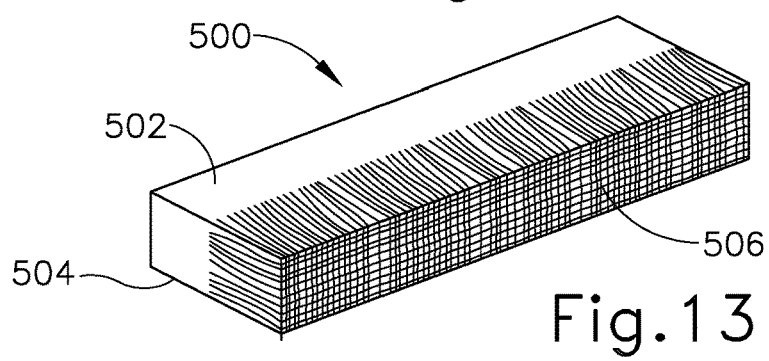
FIG. 13 depicts a perspective view of another exemplary alternative wiper seal that may be incorporated into the instrument of FIG. 7, the wiper seal having a finely-bristled edge.

As illustrated in FIGS. 10-13, wiper (200) and contacting edge (206) may comprise various shapes, profiles, and configurations. In particular, as seen in FIG. 10, wiper (200) may comprise a squared top and bottom surface (202, 204) with contacting edge (206) having a flattened face. As illustrated in FIG. 11, wiper (300) may comprise a chamfered top and bottom surface (302, 304) and a rounded contacting edge (306). Further, as shown in FIG. 12, top and bottom surfaces (402, 404) of wiper (400) may have a squared profile while contacting edge (406) has a grossly-bristled edge. In some versions of wiper (400), contacting edge (406) may include a bristle for each electrical contact on electrical connector (108). In this instance, each bristle on contacting edge (406) may be sized and shaped in accordance with the size and shape of the corresponding electrical contact. In other versions, wiper (400) may include more or fewer bristles along contacting edge (406) than the number of electrical contacts on electrical connector (108). Similarly, wiper (500) comprises a squared top and bottom surface (502, 504) with a finely-bristled contacting edge (506). As it will be apparent to those of ordinary skill in the art in view of the teachings herein, wiper (200, 300, 400, 500) and contacting edge (206, 306, 406, 506) may comprise various other suitable shapes, profiles, and configurations as would be appropriate to provide a fluid-impermeable barrier between top surface (202, 302, 402, 502) and bottom surface (204, 304, 404, 504).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A powered surgical instrument, comprising: (a) a shaft assembly, wherein the shaft assembly includes a first electrical connector and a flexible element positioned adjacent to the first electrical connector; and (b) a handle assembly, wherein the handle assembly includes a second electrical connector, wherein the handle assembly is configured to attach to the shaft assembly; wherein the second electrical connector is configured to electrically connect with the first electrical connector when the handle assembly is attached to the shaft assembly; and wherein the flexible element is configured to create a liquid-resistant seal against the handle assembly and adjacent to the electrical connection of the first and second electrical connectors when the shaft assembly and the handle assembly are attached.

Example 2

The powered surgical instrument of Example 1, wherein the flexible element is operable to separate the mating of the first and second electrical connectors from a remainder portion of the shaft assembly and the handle assembly.

Example 3

The powered surgical instrument of Example 2, wherein the flexible element comprises an end portion, wherein the end portion extends laterally along a length of the flexible element, wherein the end portion extends proximally from the shaft assembly.

Example 4

The powered surgical instrument of Example 3, wherein the end portion is configured to compress against the handle assembly when the shaft assembly couples with the handle assembly such that the flexible element creates a seal between the shaft and handle assemblies.

Example 5

The powered surgical instrument of Example 4, wherein the flexible element is configured to redirect fluid away from the first and second electrical connectors.

Example 6

The powered surgical instrument of any one or more of Examples 3 through 5, wherein the end portion is configured to clean and/or wipe the second electrical connector when the shaft assembly is being attached to the handle assembly.

Example 7

The powered surgical instrument of any one or more of Examples 3 through 6, wherein the end portion is configured to clean and/or wipe the second electrical connector when the shaft assembly is being detached from the handle assembly.

Example 8

The powered surgical instrument of any one or more of Examples 3 through 7, wherein the flexible element and end portion are formed of a hydrophobic material.

Example 9

The powered surgical instrument of any one or more of Examples 3 through 7, wherein the flexible element and end portion are coated with a hydrophobic material.

Example 10

The powered surgical instrument of any one or more of Examples 3 through 7, wherein the flexible element and end portion are formed of a water-absorptive material.

Example 11

The powered surgical instrument of any one or more of Examples 3 through 10, wherein the end portion comprises a squared profile.

Example 12

The powered surgical instrument of any one or more of Examples 3 through 10, wherein the end portion comprises a rounded profile.

Example 13

The powered surgical instrument of any one or more of Examples 3 through 10, wherein the end portion comprises a bristled profile.

Example 14

The powered surgical instrument of any one or more of Examples 2 through 13, wherein the flexible element comprises a squared profile.

Example 15

The powered surgical instrument of any one or more of Examples 2 through 13, wherein the flexible element comprises a chamfered profile.

Example 16

A powered surgical instrument, comprising: (a) a shaft assembly, wherein the shaft assembly includes a first electrical connector positioned along a first interface surface; (b) a handle assembly, wherein the handle assembly includes a second electrical connector positioned along a second interface surface, wherein the handle assembly is configured to attach to the shaft assembly; and (c) a flexible element, wherein the flexible element is positioned on the handle assembly along the second interface surface; wherein the second electrical connector is configured to electrically mate with the first electrical connector when the handle assembly is attached to the shaft assembly; wherein the flexible element is configured to create a water-resistant seal when the handle assembly attaches to the shaft assembly; and wherein the flexible element is operable to isolate the first and second electrical connectors from a remainder portion of the first and second interface surfaces when the handle and shaft assemblies attach together.

Example 17

The powered surgical instrument of Example 16, wherein the flexible element is operable to separate the first and second electrical connectors from a remainder portion of the first and second interface surfaces.

Example 18

The powered surgical instrument of any one or more of Examples 16 through 17, wherein the flexible element includes an end portion configured to create a seal against the second interface surface of the handle assembly when the shaft and handle assemblies attach together.

Example 19

The powered surgical instrument of any one or more of Examples 16 through 18, wherein the flexible element is configured to redirect fluid away from the electrical connectors, wherein the end portion is configured to clean and/or wipe the first electrical connector when the shaft assembly is attached or detached from the handle assembly.

Example 20

A method of cleaning an electrical connector of a surgical instrument, wherein the surgical instrument includes a shaft assembly and a handle assembly configured to attach together, wherein the surgical instrument includes a flexible element configured to extend from the shaft assembly, the method comprising: (a) guiding the shaft assembly onto the handle assembly; (b) contacting the flexible element against an electrical connector of the handle assembly to thereby wipe over the electrical connector; (c) attaching the shaft assembly to the handle assembly; (d) detaching the shaft assembly from the handle assembly; and (e) contacting the flexible element against the electrical connector to thereby wipe over the electrical connector.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, filed Jun. 27, 2017, entitled "Apparatus and Method to Determine End of Life of Battery Powered Surgical Instrument," filed on even date herewith, the disclosure of which is incorporated by reference herein. Various suitable ways in which the teachings herein may be combined with the teachings of U.S. patent application Ser. No. 15/634,385, filed Jun. 27, 2017 will be apparent to those of ordinary skill in the art in view of the teachings herein.

In addition to the foregoing, the teachings herein may be readily combined with the teachings of U.S. patent application Ser. No. 15/634,418, filed Jun. 27, 2017, entitled "Surgical Instrument with Integrated and Independently Powered Displays," filed on even date herewith, the disclosure of which is incorporated by reference herein. Various suitable ways in which the teachings herein may be combined with the teachings of U.S. patent application Ser. No. 15/634,418, filed Jun. 27, 2017 will be apparent to those of ordinary skill in the art in view of the teachings herein.

In addition to the foregoing, the teachings herein may be readily combined with the teachings of U.S. patent application Ser. No. 15/634,436, filed Jun. 27, 2017, entitled "Battery Pack with Integrated Circuit Providing Sleep Mode to Battery Pack and Associated Surgical Instrument," filed on even date herewith, the disclosure of which is incorporated by reference herein. Various suitable ways in which the teachings herein may be combined with the teachings of U.S. patent application Ser. No. 15/634,436, filed Jun. 27, 2017 will be apparent to those of ordinary skill in the art in view of the teachings herein.

In addition to the foregoing, the teachings herein may be readily combined with the teachings of U.S. patent application Ser. No. 15/634,452, filed Jun. 27, 2017, entitled "Battery Powered Surgical Instrument with Dual Power Utilization Circuits for Dual Modes," filed on even date herewith, the disclosure of which is incorporated by reference herein. Various suitable ways in which the teachings herein may be combined with the teachings of U.S. patent application Ser. No. 15/634,452, filed Jun. 27, 2017 will be apparent to those of ordinary skill in the art in view of the teachings herein.

In addition to the foregoing, the teachings herein may be readily combined with the teachings of U.S. patent application Ser. No. 15/634,475, filed Jun. 27, 2017, entitled "Powered Surgical Instrument with Latching Feature Preventing Removal of Battery Pack," filed on even date herewith, the disclosure of which is incorporated by reference herein. Various suitable ways in which the teachings herein may be combined with the teachings of U.S. patent application Ser. No. 15/634,475, filed Jun. 27, 2017 will be apparent to those of ordinary skill in the art in view of the teachings herein.

In addition to the foregoing, the teachings herein may be readily combined with the teachings of U.S. patent application Ser. No. 15/634,497, filed Jun. 27, 2017, entitled "Modular Powered Electrical Connection for Surgical Instrument with Features to Prevent Electrical Discharge" filed on even date herewith, the disclosure of which is incorporated by reference herein. Various suitable ways in which the teachings herein may be combined with the teachings of U.S. patent application Ser. No. 15/634,497 filed Jun. 27, 2017 will be apparent to those of ordinary skill in the art in view of the teachings herein.

In addition to the foregoing, the teachings herein may be readily combined with the teachings of U.S. patent application Ser. No. 15/634,524, filed Jun. 27, 2017, entitled "Powered Surgical Instrument with Independent Selectively Applied Rotary and Linear Drivetrains," filed on even date herewith, the disclosure of which is incorporated by reference herein. Various suitable ways in which the teachings herein may be combined with the teachings of U.S. patent application Ser. No. 15/634,524, filed Jun. 27, 2017 will be apparent to those of ordinary skill in the art in view of the teachings herein.

In addition to the foregoing, the teachings herein may be readily combined with the teachings of U.S. patent application Ser. No. 15/634,556, filed Jun. 27, 2017, entitled "Powered Circular Stapler with Reciprocating Drive Member to Provide Independent Stapling and Cutting of Tissue," filed on even date herewith, the disclosure of which is incorporated by reference herein. Various suitable ways in which the teachings herein may be combined with the teachings of U.S. patent application Ser. No. 15/634,556, filed Jun. 27, 2017 will be apparent to those of ordinary skill in the art in view of the teachings herein.

In addition to the foregoing, the teachings herein may be readily combined with the teachings of U.S. patent application Ser. No. 15/634,620, filed Jun. 27, 2017, entitled "Surgical Stapler with Independently Actuated Drivers to Provide Varying Staple Heights," filed on even date herewith, the disclosure of which is incorporated by reference herein. Various suitable ways in which the teachings herein may be combined with the teachings of U.S. patent application Ser. No. 15/634,620, filed Jun. 27, 2017 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A powered surgical instrument, comprising:
   (a) a shaft assembly, wherein the shaft assembly includes a first electrical connector and a flexible element positioned adjacent to the first electrical connector; and
   (b) a handle assembly, wherein the handle assembly includes a second electrical connector, wherein the handle assembly is configured to attach to the shaft assembly;
   wherein the second electrical connector is configured to electrically connect with the first electrical connector when the handle assembly is attached to the shaft assembly; and
   wherein the flexible element is configured to create a liquid-resistant seal against the handle assembly and adjacent to the electrical connection of the first and second electrical connectors when the shaft assembly and the handle assembly are attached, wherein the flexible element is operable to separate the mating of the first and second electrical connectors from a remainder portion of the shaft assembly and the handle assembly.

2. The powered surgical instrument of claim 1, wherein the flexible element comprises an end portion, wherein the end portion extends laterally along a length of the flexible element; wherein the end portion extends proximally from the shaft assembly.

3. The powered surgical instrument of claim 2, wherein the end portion is configured to compress against the handle assembly when the shaft assembly couples with the handle assembly such that the flexible element creates a seal between the shaft and handle assemblies.

4. The powered surgical instrument of claim 3, wherein the flexible element is configured to redirect fluid away from the first and second electrical connectors.

5. The powered surgical instrument of claim 2, wherein the end portion is configured to clean and/or wipe the second electrical connector when the shaft assembly is being attached to the handle assembly.

6. The powered surgical instrument of claim 2, wherein the end portion is configured to clean and/or wipe the second electrical connector when the shaft assembly is being detached from the handle assembly.

7. The powered surgical instrument of claim 2, wherein the flexible element and end portion are formed of a hydrophobic material.

8. The powered surgical instrument of claim 2, wherein the flexible element and end portion are coated with a hydrophobic material.

9. The powered surgical instrument of Therein the flexible element and end portion are formed of a water-absorptive material.

10. The powered surgical instrument of claim 2, wherein the end portion comprises a squared profile.

11. The powered surgical instrument of claim 2, wherein the end portion comprises a rounded profile.

12. The powered surgical instrument of claim 2, wherein the end portion comprises a bristled profile.

13. The powered surgical instrument of claim 1, wherein the flexible element comprises a squared profile.

14. The powered surgical instrument of claim 1, wherein the flexible element comprises a chamfered profile.

15. A powered surgical instrument, comprising:
(a) a shaft assembly, wherein the shaft assembly includes a first electrical connector positioned along a first interface surface;
(b) a handle assembly, wherein the handle assembly includes a second electrical connector positioned along a second interface surface; wherein the handle assembly is configured to attach to the shaft assembly; and
(c) a flexible element, wherein the flexible element is positioned on the handle assembly along the second interface surface;
wherein the second electrical connector is configured to electrically mate with the first electrical connector when the handle assembly is attached to the shaft assembly;
wherein the flexible element is configured to create a water-resistant seal when the handle assembly attaches to the shaft assembly; and
wherein the flexible element is operable to isolate the first and second electrical connectors from a remainder portion of the first and second interface surfaces when the handle and shaft assemblies attach together.

16. The powered surgical instrument of claim 15, wherein the flexible element is operable to separate the first and second electrical connectors from a remainder portion of the first and second interface surfaces.

17. The powered surgical instrument of claim 15, wherein the flexible element includes an end portion configured to create a seal against the second interface surface of the handle assembly when the shaft and handle assemblies attach together.

18. The powered surgical instrument of claim 15, wherein the flexible element is configured to redirect fluid away from the electrical connectors, wherein the end portion is configured to clean and/or wipe the first electrical connector when the shaft assembly is attached or detached from the handle assembly.

19. A method of cleaning an electrical connector of a surgical instrument, wherein the surgical instrument includes a shaft assembly and a handle assembly configured to attach together, wherein the surgical instrument includes a flexible element configured to extend from the shaft assembly, the method comprising:
(a) guiding the shaft assembly onto the handle assembly;
(b) contacting the flexible element against an electrical connector of the handle assembly to thereby wipe over the electrical connector;
(c) attaching the shaft assembly to the handle assembly;
(d) detaching the shaft assembly from the handle assembly; and
(e) contacting the flexible element against the electrical connector to thereby wipe over the electrical connector.

* * * * *